United States Patent [19]
Brandsma

[11] Patent Number: 5,811,632
[45] Date of Patent: Sep. 22, 1998

[54] NON-HUMAN MAMMALIAN MODEL FOR HUMAN PAPILLOMAVIRUS-INDUCED DISEASE

[76] Inventor: Janet L. Brandsma, P.O. Box 208016, New Haven, Conn. 06520-8016

[21] Appl. No.: 311,803

[22] Filed: Sep. 26, 1994

[51] Int. Cl.$^6$ .............................. C12N 5/00; C12N 15/00; A61K 48/00
[52] U.S. Cl. ...................... 800/2; 800/DIG. 5; 435/172.3; 424/9.1
[58] Field of Search .................................. 800/2, DIG. 5; 435/172.3; 424/574, 9.1

[56] References Cited

PUBLICATIONS

Brandsma, J.L., et al., "HPV DNA Induces Papilloma in Human Skin Grafted on Mice," poster and talk presented at 12th International Papillomavirus Conference (1993).

Brandsma, J.L., and W. Xiao, "Infectious Virus Replication in Papillomas Induced by Molecularly Cloned Cottontail Rabbit Papillomavirus DNA," *Journal of Virology,* 67:567–571 (1993).

Defeo–Jones, D., et al., "Papillomairus E7 Protein Binding to the Retinoblastoma Protein Is Not Required for Viral Induction of Warts," *Journal of Virology,* 67:716–725 (1993).

Koller, L. D., and C. Olson, "Attempted Transmission of Warts from Man, Cattle, and Horses and of Deer Fibroma, to Selected Hosts," *Journal of Investigative Dermatology,* 58:366–368 (1972).

Kreider, J. W., et al. "Morphological Transformation In Vivo of Human Uterine Cervix with Papillomavirus from Condylomata Acuminata," *Nature* 317:639–641 (1985).

Krider, J. W., et al., "In Vivo Transformation of Human Skin with Human Papillomavirus Type 11 from Condylomata Acuminata," *Journal of Virology,* 59:369–376 (1986).

Kreider, J. W., et al., "Susceptibility of Various Human Tissues to Transformation In Vivo with Human Papillomavirus Type 11," *Int. J. Cancer,* 39:459–465 (1987a).

Kreider, J. W., et al., "Tissue–specific Expression of Human Papillomavirus Type 11," *Cancer Cells 5/Papillomaviruses,* 215–221 (1987b).

Krider, J.W., and M. K. Howett, "Human Papillomavirus–11 Infection of Xenografted Human Tissues," pp. 371–385 in *Viruses and Human Cancer,* Alan R. Liss, Inc. (1987).

Nasseri, M., et al., "Genetic Analysis of CRPV Pathogenesis: The L1 Open Reading Frame Is Dispensable for Cellular Transformation but Is Required for Papilloma Formation," *Virology,* 170:321–325 (1989).

Sterling, J., et al., "Production of Human Papillomavirus Type 16 Virions in a Keratinocyte Cell Line," *Journal of Virology,* 64:6305–6307 (1990).

Wettstein, F. O., "State of Viral DNA and Gene Expression in Benign Vs. Malignant Tumors," pp. 155–179 in *Papillomaviruses and Human Cancer,* ed. Herbert Pfister, CRC Press, Inc., Boca Raton (1990).

*Primary Examiner*—Deborah Crouch
*Attorney, Agent, or Firm*—Robins & Associates

[57] ABSTRACT

A method for producing a mammalian model for papillomavirus infection by engrafting a portion of human skin onto a transplant-tolerant non-human mammal, inoculating the engrafted human skin with a papillomavirus genomic DNA such that a papillomavirus infection develops in the engrafted human skin or human skin cells. The non-human mammals are then used to identify compounds and therapies effective against papillomavirus infections.

28 Claims, No Drawings

NON-HUMAN MAMMALIAN MODEL FOR HUMAN PAPILLOMAVIRUS-INDUCED DISEASE

STATEMENT REGARDING FEDERALLY-SPONSORED RESEARCH

This invention was made with United States Government support under grants number R03-CA 54978 and RO1-CA 57970. The United States Government has certain rights in this invention.

FIELD OF THE INVENTION

The present invention relates to a model system that enables in vivo development in animals of therapeutic strategies for overcoming or preventing virus infections in human skin. More particularly, the invention relates to a mouse model for induction of human papillomavirus disease in human skin.

BACKGROUND OF THE INVENTION

Infection of the anogenital tract with high risk human papillomaviruses (HPV) causes benign intraepithelial neoplasias that, after an extended latent period, can become dysplastic and eventually progress to invasive squamous cell or adenocarcinomas. Anogenital infections are common in sexually active women and men, and a significant proportion are due to high risk HPVs. Each year, about 500,000 such infections undergo malignant conversion at the uterine cervix, making cervical cancer the most common malignancy in women world-wide. About 90 percent of such tumors contain high risk HPVs, with HPV type (HPV16) being most prevalent. High risk HPVs have also been associated with squamous cell carcinomas of the vulva, vagina, anus and penis, as well as with some head and neck cancers.

High risk HPVs fall within the larger class of human tumor viruses, which share a characteristic ability to transform cells in culture. An association of several human tumor viruses, including HPVs, with particular human cancers has also been shown, though the modes of action of such viruses, and their roles in carcinogenesis, are, in large part, unclear. Other than HPV, the other cancer-associated human tumor viruses and their associated malignancies are human T-cell leukemia virus (HTLV; in rare T-cell lymphomas), Hepatitis B Virus (HBV; in hepatomas), Epstein-Barr Virus (EBV; in Burkitt's Lymphoma and nasopharyngeal carcinoma). Human immunodeficiency virus (HIV) is associated with various malignancies found in AIDS patients.

To determine the pathogenesis of virus-associated cancers and premalignant lesions and to develop effective strategies for their prevention or treatment in humans, it is imperative to have a satisfactory animal model system. Early efforts at inducing HPV disease in animals by direct inoculation of virus have not proved reproducible.

Previously, a nonhuman animal model was developed for HPV11, a low risk genital virus not associated with cancer. Human foreskin chips were incubated in vitro with virus obtained from *condylomata acuminata*, an HPV-induced human lesion, and transplanted under the renal capsule of athymic mice, or, more recently, in the subcutis or peritoneum of severe combined immunodeficient (scid) mice. Infected tissue developed into virus-producing condylomatous cysts, which model has proved useful for studying the infectious life cycle of HPV11. This approach has also been adapted to HPV1, a cause of plantar warts. Infectious mutants of HPV11 (or of HPV1) have, however, not been described, and the functions of individual viral genes in this model have not been determined. The model may also not be applicable to high risk HPVs because of the lack of a source of infectious virus. Natural lesions induced by high risk HPVs appear not to produce significant amounts of virus.

Another mouse model was developed by grafting onto the backs of athymic mice human W12 keratinocytes that had been established from a natural HPV16 infection. W12 cells, in which HPV16 DNA persisted in an episomal state, differentiated to form an epithelium with morphologic features of a low-grade HPV lesion. Some grafts expressed HPV capsid antigen and produced viral particles, an effect that correlated with the episomal nature of the viral genome. Because most cell lines derived from natural infections contain only integrated HPVs, the applicability of this approach for generating a panel of engrafted animals expressing a variety of HPV types appears to be limited. The model also does not lend itself to analysis of viral mutants.

In the absence of an optimal animal model for high risk HPV disease, the identification of biological activities and biochemical properties of HPV genes and cis-acting elements has relied almost exclusively on in vivo systems. The importance of these functions for the induction and progression of actual disease, however, remains largely unknown. Infectious viral progeny can also not be propagated in cultured cells, so infectious stocks of virus and virus mutants are not available. Additionally, the vegetative replication strategy of papillomaviruses is poorly understood.

An animal model exists that permits experimental induction of benign viral papillomas that can progress to squamous cell carcinoma upon inoculation of rabbits with molecular clones of the Shope or cottontail rabbit papillomavirus (CRPV). This model has been used to identify viral genes required for papilloma induction. The model has also been used to produce infectious virus stocks. In the rabbit model, CRPV DNA has been inoculated into rabbit skin using a high pressure jet injector method, or by tedious manual scarification.

SUMMARY OF THE INVENTION

The present invention is summarized in that exophytic papillomas with the histopathologic characteristics of papillomavirus infection, including koilocytosis and capsid antigen synthesis, may be induced in human genital skin by delivering DNA copies of an HPV viral genome into human genital skin engrafted onto a transplant-tolerant nonhuman, eukaryotic animal. Induction of HPV lesions in a model animal permits the testing of prophylactic and therapeutic agents and facilitates investigation of HPV viral functions that may serve as molecular targets.

The present invention is also summarized in that pathogenic effects induced by other viruses that infect human skin may be induced in human skin by delivering copies of the other viral genomes into human skin engrafted onto a transplant-tolerant nonhuman, eukaryotic animal.

It is yet another object of the present invention to provide a nonhuman animal model in which the biology of human skin viruses may be examined.

It is an object of the present invention to provide a nonhuman animal model system in which HPV- and other virus-specific diseases may be reproducibly induced.

It is another object of the present invention to provide a nonhuman animal model in which various prophylactic and therapeutic anti-viral agents may be tested.

It is a feature of the present invention that to produce a viral papilloma, a molecular DNA clone of the HPV genome is delivered to the human genital skin after engraftment of the skin onto the nonhuman animal.

It is feature of the present invention that mutant viral genomes may be used to identify molecular targets for therapeutic intervention.

It is another feature of the present invention that the nonhuman animal receiving the human genital skin is unable to mount an adequate immune response to reject the engrafted human genital tissue.

It is yet another advantage of the present invention that because the animal receiving the human genital skin graft is immunocompromised, the latency period during which benign HPV-induced viral lesions convert to malignant carcinomas may be shortened.

It is yet another advantage of the present invention that because the animal receiving the human genital skin graft is immunocompromised, it can be adoptively transferred with immunocompetent cells prior to or after induction of disease. In this way, it may be possible to determine the nature of the immune response required to protect from infection or disease or to induce regression of established disease. Artificial induction of such a response could lead to an effective prophylactic or therapeutic HPV vaccine or other immunotherapy.

It is an advantage of the present invention that the experimental induction of high risk HPV disease on human skin permits the controlled testing of prophylactic and therapeutic anti-HPV agents directed toward controlling high risk HPV infection and toward preventing conversion of benign lesions to malignant cancers where no such testing vehicle now exists.

It is a further advantage of the present invention that the experimental induction of macroscopic disease can be monitored without sacrifice of the animal.

It is a further advantage of the present invention that the experimental induction of HPV lesions permit the controlled examination of all aspects of the biology of HPV in one of its natural host tissues, human genital skin.

It is a still further advantage of the present invention that viral replication in DNA-induced lesions facilitates the experimental production of genotype-specific and replication-competent mutant viral stocks.

Other objects, advantages and features of the present invention will become apparent upon consideration of the following specification.

DETAILED DESCRIPTION OF THE INVENTION

The present invention is directed to a method for generating an animal model for inoculating human skin with human papillomaviruses, and to animals that model the effects of human papillomavirus infection. Such animals are desired in that no satisfactory model for high risk HPV disease now exists. Direct infection of nonhuman species with HPVs does not induce disease. It has been impossible, therefore, to perform controlled studies on disease development, disease progression or regression, and on prevention or treatment of diseases induced in humans by high risk HPVs. It has also been impossible to determine which viral gene effects cause which aspects of the pathogenetic processes. More generally, the invention is also directed to a method for generating an animal model for studying the biology of normal and abnormal human skin, for infecting human skin with viruses that induce pathologic effects in humans, and to the infectable animals produced.

In accordance with the invention, a satisfactory animal for use in such studies is produced by first grafting onto a plurality of nonhuman eukaryotic animals a portion of human skin capable of exhibiting viral-induced disease effects and possibly supporting permissive viral growth. Biologically active viral DNA is inoculated into the grafted cells or tissues, before or after engraftment, preferably by particle acceleration. After waiting a period of time sufficient to permit the expression of the inoculated viral DNA, it is possible to screen the plurality of host animals to choose those animals that manifest a viral infection.

At present at least 70 human papillomaviruses are known, of which several have been causally associated with human cervical and other anogenital carcinomas and some head and neck cancers. It is envisioned that the model system disclosed herein will have utility in investigation of HPV gene functions which will then suggest avenues for prophylactic and therapeutic intervention against both benign and malignant lesions, including invasive squamous cell carcinomas. It is therefore envisioned that, in addition to DNA from high risk HPV types, viral DNAs from low risk HPVs, obtained from in vivo or in vitro sources, may also be inoculated into human tissue grafts. Appropriate viral DNAs could also derive from variants of known viruses that have been generated in vivo or in vitro.

Also, DNA from any non-HPV virus that can infect and cause pathologic effect in human skin is appropriately delivered to a xenograft in accord with the present invention to produce a model animal infected with the chosen virus. Such viruses include Epstein-Barr virus, Herpes simplex viruses, varicella zoster, and dengue virus. It is a specific advantage of the method described here that isolated DNA from the virus is used for the procedure, rather than whole virus. The isolated viral DNA must have the genetic components from the virus necessary for the viral disease process, and can be whole viral genomic DNA, or genomic DNA truncated or modified to remove genetic sequences not necessary for the disease process. The viral genomic DNA can be isolated directly from culture of the virus, or can be transferred into a bacterial vector for replication for use in the procedure. In the example below, for reasons of convenience, a vector harboring the HPV16 DNA was used, but it should be apparent to those skilled in the art that this strain has no unique properties as concerns the procedure described here, and hence DNA from any other HPV strain may be substituted in the procedure with similar result.

An animal appropriate for use in this method is any transplant-tolerant nonhuman eukaryotic animal which is an animal that can accept and maintain a human xenograft of tissue or cells in a healthy state. It is desirable that the animal be chosen to share basic physiological and biochemical similarity with humans, so that data obtained in tests performed on the animals produced by the method may be rationally extrapolated to humans. Moreover, since relatively large numbers of animals are required for testing of anti-HPV therapeutic agents, it would also be advantageous for the animals to be relatively small, to reduce housing and food costs. For these reasons, the preferred host animals are mammals, most especially the rodents such as mice and rats.

While it will be generally understood that no tissue graft protocol offers 100% success, it is preferable that the host be able to accept and maintain more than 50%, and most preferably, more than 80%, of the attempted grafts so that an appreciable number of control and virus-positive, engrafted animals may be obtained at minimal cost.

Xenografts are rejected by a host animal when the animal's immune system recognizes the graft as foreign. Graft rejection is not compatible with the present invention. Therefore, a desired host animal is unable to recognize the xenograft as foreign; rather, a desired host accepts the graft as "self." In eukaryotes, immune system recognition is mediated by a combination of a blood-borne antibody-based immune system and a cell-mediated immune system, each of which has particular specialized functions. The art is cognizant of several agents, such as drugs and radiation, that can eliminate the functions of one or both immune systems in individual animals, but these agents may induce other deleterious effects on the animals and the effects of these agents may diminish over time. For these reasons, the preferred host is genetically incapable of mounting a graft-rejecting immune response. Most preferably, both the circulating and cell-mediated immune responses are eliminated, although it is possible to maintain a graft in an animal lacking only the cell-mediated immune system. While these incapabilities can arise from independent genetic mutations, which may be bred together to produce a desired host, there is known a single mutation in mice that results in a severe combined immunodeficiency, or "scid," phenotype. Mice bred to be homozygous scid/scid completely lack both components of the normal immune system. This mutation has been bred onto popular genetic backgrounds and such mice are now commercially available from, for example Taconic Quality Laboratory Animals for Research, Germantown, N.Y. Accordingly, scid/scid mice are a preferred host for receiving a human tissue graft. The scid mutation in the mouse is described in Bosma G.C., et al., "A severe combined immunodeficiency mutation in the mouse" 301 *Nature* 527–530 (1983). Alternatively, athymic "nude" mice and rats that lack a cell-mediated immune system are believed to be useful in the method as hosts for the human skin graft.

In each case, the engrafted target skin tissue preferably corresponds to a natural infection site of the virus being tested, to maximize the likelihood of viral transcription and translation and appropriate virus-host cell interactions in the grafted skin cells. The human skin grafted onto the animal should support in vivo transcription and translation of inoculated viral DNA such that the grafted tissue can acquire the characteristic morphological, biochemical and histological features of viral infection. In the preferred case of human papillomavirus infection, the notable hallmarks of infection include papillomatous morphology, histopathology, altered cellular differentiation, and detectable levels of viral DNA. While it is possible that, under defined conditions, many types of human skin could support viral expression, it is advantageous that the human tissue used be a known, natural target for the infecting virus. It is also advantageous that the human skin chosen be readily available so that large numbers of model animals may be produced. It is further advantageous that the human tissue be suitable for transplantation at the location of external mouse skin to enable constant visual monitoring. A preferred human tissue for use in the human papillomavirus model, having both of these desirable traits, is the male foreskin. Being a genital tissue, the foreskin is susceptible to infection by human genital papillomaviruses. Moreover, hospitals can provide a ready source of a large number of foreskins, which are frequently removed from newborn males in an elective procedure soon after birth and which would otherwise be discarded. Other tissues that are natural targets for HPV infection and that are believed by the inventors to be useful in the present method are cervical, vaginal, vulval, anal, perianal tissue and vocal cords.

The grafts may be performed according to standard aseptic grafting protocols known to the art. Typically, a human skin sample of about 10×10 mm is appropriate for grafting onto a comparable sized site on the animal. Preferably, the human skin may be prepared by removing excess underlying dermis. The animal should be anesthetized and the graft site prepared by hair removal and disinfection. At that point, the animal's skin may be excised, the fascia removed, and the muscle preferably wounded. The human tissue can then be transplanted to the site and held in place initially with wound clips or sutures. Initially, necrosis of the grafted tissue is typical, though the necrotic period is followed by a healing period, after which, the graft assumes the appearance of normal human skin.

To inoculate the viral DNA into the graft cells, it is preferred that a particle acceleration device, such as that described in U.S. Pat. No. 5,015,580, be employed. U.S. Pat. No. 5,015,580 which also details a method for delivering copies of a genetic construct into a target is incorporated herein by reference.

DNA delivered by particle acceleration is coated onto dense metal particles, such as gold powder, which coated particles are directed into cells by means of an accelerating force.

It is important then that a force be used that is high enough to penetrate the human cells, preferably in the basal cell layer, yet is not so high that the DNA passes through the cells and into the tissue beneath the grafted epidermis. A preferred apparatus for delivery is an Agracetus ACCELL ® gene gun in which an electric spark discharge of adjustable force accelerates a planar carrier sheet toward the target tissue. On the carrier sheet are deposited the DNA coated particles. During acceleration, movement of the carrier sheet is impeded, although the coated particles detach from the carrier sheet and continue to accelerate toward and into the target. It has been found that a preferred discharge voltage ranges from 15 to 25 kV, and is most preferably 20 kV. Voltages within these ranges deliver the DNA-coated particles into the target epidermis but cause no damage to the target tissue.

Although accelerated particle delivery is preferred for its increased gene delivery frequency, other means for delivering DNA into the engrafted target tissue are also possible. These delivery means can include, for example, transdermal patch, ointment, lotion, gel, salve, cream, spray or the like. Compositions for delivering genetic constructs could also include a delivery-enhancing agent such as, for example, dimethylsulfoxide (DMSO), which is known to increase the permeability of cell membranes to genetic material.

After inoculation, the grafts are observed for signs of viral infection. The duration of the latent period between inoculation and appearance of viral infection may vary depending upon the strain of inoculant, the source of human skin, the genetic background of the host, the delivery method or other factors. In addition, using visual examination, it may be difficult to detect extremely small lesions. In the preferred embodiment, for example, several weeks passed before lesions were detectable on human foreskin engrafted to scid/scid mice. No lesions were detectable at 35 days post-inoculation, but lesions were detectable after 8 or 9 weeks. It is preferred, therefore, that at least five weeks, and more preferably at least eight weeks, pass before sacrificing the animals for histologic and biochemical evaluation of HPV viral infection.

It has also been found by the present inventors that viral infection has been observed only in grafts that were inoculated after the graft was in place on the host and past the necrotic stage. In cases where the human tissue was inoculated and then engrafted onto the animal, no virus effects was observed. It may be that a block arises which prevents the viral genome from becoming established in such grafts, such as an inadequate viability, possibly due to an insufficient blood supply to the graft at the immediate post-transplantation stage. Such a block may be surmountable by appropriate additional treatments, e.g. administration of growth factors.

After inoculation, the animals are monitored for visual or palpable lesions. The diagnosis of experimental HPV lesions, like that of naturally occurring HPV lesions, also requires histopathologic examination. In addition, DNA studies are important for determining that a particular animal has been infected. For instance, it is apparent from the observations detailed in the Example, below, that the human skin xenografts of some animals exhibited morphologic and histologic lesions characteristic of HPV infection and that the infection was induced by inoculation with biologically active HPV DNA. According, animals produced in accord with the invention may be reliably considered to be a satisfactory model system for evaluating the efficacy of potential therapeutic agents for use in humans to treat virus-induced disease.

Having now been provided with a satisfactory model animal, one of ordinary skill in the art is able to envision an array of potential therapeutic agents and delivery protocols for testing. For example, the potential anti-HPV and anti-tumor agents may be natural products or synthetic molecules of human design. Moreover, the model provides a vehicle for selection of effective agents from among a battery of known and novel compounds. The dosage and delivery mode of any particular potential therapeutic agent can be determined on the basis of well established guidelines for preparing pharmaceutically active compositions. The test compounds may be administered, for example, intravenously, intradermally, intramuscularly, topically, orally, or by any other pharmaceutically effective route. Using the animals produced by the method of the present invention, an investigator can now, for the first time, evaluate prophylactic and therapeutic agents against high risk human papillomavirus-induced disease, possibly including virus replication and transmission. These may include, among others, chemical-type pharmaceuticals, genetic therapies, antisense inhibitory strategies, or prophylactic or therapeutic vaccination. Many methods of evaluating the results of laboratory tests of proposed therapeutics are known.

Another class of investigation made possible by the method of the present invention is the study of genetic mutant viruses. Since the process envisions the use of isolated viral DNA, it becomes possible to intelligently or randomly alter the viral DNA prior to insertion into the human skin to examine any changes in disease process or timing created by such alterations. Such mutant studies can be used to investigate minimal viral components necessary for disease induction or progression or may suggest targets for therapeutic intervention. The mutations tested can be selective and site-directed or can be random and could include sequence insertion, deletion, truncation or modification.

The invention may be more clearly understood by reference to the following example, which is intended to be purely exemplary of the method of the present invention.

EXAMPLE

Foreskins were obtained after routine circumcision of newborn human males. The underlying dermis was partially removed with scissors and the epidermis was cut into squares approximately 10×10 mm. Each foreskin yielded two or three such squares.

Fox Chase C.B17 scid/scid Pneumocystis carinii-free, 5–8 week old mice (obtained from Taconic) were selected as graft recipients on the basis of their complete lack of circulating and cell-mediated immune systems. Severe combined immunodeficient (scid) mice can receive both allogenic and xenogenic grafts, including skin grafts.

Foreskin samples were grafted onto the back of each recipient mouse, typically within three hours of the circumcision. The mice were anesthetized by intraperitoneal injection of a mixture of Ketamine (94 mg) and Xylazine (94 mg) per 30 g of body weight. The autologous mouse skin was clipped free of hair and surgical sites were disinfected. Using aseptic technique, the autologous mouse skin was excised and prepared as described. A comparable sized piece of newborn human foreskin, prepared as described, was engrafted onto the site and held in place with wound clips or sutures. In the first week following engraftment, the human foreskin xenografts underwent mild necrosis and appeared darkened and encrusted. However, gradually over a three week period, the necrotic crusts were lost and the grafts appeared as healthy human skin.

HPV DNA delivered into the experimental group of xenografts was derived from the W12 human cervical keratinocyte cell line, which contains a biologically active episomal HPV genome. The W12 cell line is described in Stanley, M.A., et al., 43 *Int. J. Cancer* 672–676 (1989). An HPV16 genome had previously been cloned from the W12 cell line in plasmid vector pSP64 and was used as the source of HPV DNA in these examples. HPV DNA was isolated from the pSP64 vector by BamHI digestion. A genome-sized DNA fragment was purified by electrophoresis in an agarose gel (0.8%) and was recircularized by ligation. Brandsma, J. L. and W. Xiao, 67 *J. Virol.* 567–571 (1993). Other molecular clones of HPVs are available.

DNA delivery was performed by particle acceleration. The HPV DNA was, therefore, prepared as follows for delivery using an Accell® particle acceleration device (Agracetus). Quantities of the recircularized, supercoiled HPV16 genomic DNA prepared as described above were reproduced in vitro. Copies of the DNA of this plasmid were then precipitated onto gold carrier particles before delivery into the xenograft. This was done by mixing 5 µg of DNA with 20 mg of gold powder (0.95 micron average diameter) in 0.2 ml $H_2O$. Then, 800 microliters of 0.25M $CaCl_2$, 12.5% PEG-6000 was added to the mixture, while continuously agitating, after which the coated gold carrier particles were permitted to precipitate. The supernatant was removed and the carrier particles were washed gently with 1 ml ethanol and resuspended in ethanol at 20 mg/ml in a glass capped vial.

The DNA-coated carrier particles were then layered onto 324 millimeter square mylar sheets (1.8 cm on each side) at a density of 6.4 mg of gold (1.6 µg DNA) per sheet. This was done by applying the ethanol suspension of the carrier particles onto the carrier sheet and then allowing the gold to settle for several minutes, after which the ethanol meniscus was broken, the ethanol was removed by pipette, and this residual ethanol was allowed to evaporate. The Mylar sheets were then dried under a heat lamp. The DNA-coated gold particles on each mylar sheet were then placed in an Agracetus Accell® accelerated particle transformation apparatus of the type described in U.S. Pat. No. 5,015,580, which utilizes an adjustable electric spark discharge to accelerate the carrier particle at the target cells to be transfected by the carrier DNA. Meanwhile, the engrafted animals were positioned below (hand held device) the accelerated particle apparatus and gene delivery was performed using a discharge voltage between 15 and 25 kV, preferably 20 kV.

The naked HPV16 DNA was inoculated directly into the human tissue grafts on eight recipient mice. Of the eight grafts which received DNA after engraftment and healing, seven survived and were monitored weekly for proliferative lesions. Two of the seven grafts exhibited signs suggestive of HPV infection. One developed a pronounced rough, warty feel and appearance with white exophytic projections. This graft also exhibited histologic features of papillomavirus infection, including pronounced epidermal hyperplasia, papillomatosis, acanthosis, parakeratosis, hypergranulosis and koilocytosis. A second graft displayed a series of small multifocal lesions with slightly roughened surfaces. The histologic features of this graft were also suggestive of papillomavirus infection and included epidermal hyperplasia, acanthosis, and hypergranulosis. These two grafts were derived from different foreskin donors and were engrafted onto different mice. Each of the foreskins that gave rise to the lesions had been successfully grafted at two sites on a mouse. In each case, one of the two grafts appeared completely normal, macroscopically and microscopically, demonstrating that there was no pre-existing HPV infection in the target tissue and that penetration and/or expression of HPV DNA was not universal.

A second set of DNA inoculations were performed in which HPV16 DNA was inoculated directly into human foreskin tissues before the tissues were engrafted onto eight recipient mice as described. Four of these post-inoculation grafts survived the engrafting procedure. None developed obvious HPV lesions.

HPV16 DNA was also present in the graft that formed the larger lesion. Using the polymerase chain reaction (PCR), HPV DNA sequences were amplified from DNA samples extracted from paraffin sections of the graft. The HPV-specific PCR primers (MY09 and MY11) used were described in Ting, Y. and M. Manos, "Detection and typing of genital human papillomavirus," in *PCR Protocols: A guide to methods and applications*, Academic Press: San Diego, Innis, M., et al., eds., 354–367 (1990). The PCR product was approximately 450 base pairs, as expected, and displayed HinfI and PstI restriction patterns that are characteristic of HPV16 and HPV18, but not of other HPV types. Hybridization of the PCR product to oligonucleotide HPV type specific probes for HPV16 and HPV18 demonstrated that the DNA was HPV16 and not HPV18.

Immunohistochemistry for papillomavirus group-specific antigen, a component of the virion, was performed as detailed in Kurman, R. J., et al., "Papillomavirus infection of the cervix: I. Correlation of histology with viral structural antigens and DNA sequences", 1 *Int. J. Gynecol. Pathol.* 17–28 (1982). This analysis revealed the presence of papillomavirus capsid antigens in the nuclei of the cells of the intermediate layers of one lesion. Positive nuclei were distributed in cells of the maturing epithelial layers. As expected, no viral capsid antigen was detected in the untransformed graft that derived from the same foreskin as its transformed counterpart.

Taken together, these analyses demonstrate that inoculation of HPV16 DNA was responsible for the morphologic and histologic transformation of the human foreskin graft tissue. These observations also suggest that the full life cycle of virus replication may be achieved using the process disclosed herein.

As a control, forty-four successful human foreskin grafts (out of 45 attempts) were studied. No HPV DNA was delivered to these control grafts, and none developed any signs of HPV infection. Grafts were hairless, and those derived from pigmented skin retained their pigmentation, which contrasted with the albino skin of the recipient mice. Other evidence also indicated that the grafts consisted of human skin. Involucrin was detected in maturing suprabasal keratinocytes of the human grafts by immunohistochemistry using polyclonal antiserum. Involucrin is a precursor of the epithelial envelope that is made in differentiating suprabasal cells of stratified squamous epithelia of normal human skin. Mouse proteins do not cross react with antibodies to human involucrin, and adjacent mouse skin was negative. Additionally, in situ hybridization to an oligonucleotide probe of human Alu sequences showed that the grafts contained epidermal, dermal, and adnexal cells of human origin. Nuclei of keratinocytes, sebaceous glands, apocrine sweat glands, and dermal fibroblasts hybridized to the Alu probe. Cells of mouse origin did not hybridize to the Alu probe, consistent with previous reports.

It is to be understood that the present invention is not limited to the particular embodiments disclosed in this application, but embraces all such modified forms thereof as come within the scope of the following claims.

I claim:

1. A method for producing a mammalian model for papillomavirus infection, the method comprising:
   providing a transplant-tolerant non-human mammal;
   excising from the mammal a portion of skin at a graft site;
   engrafting a portion of human skin or human skin cells into the graft site, wherein the human skin or human skin cells are not infected with papillomavirus;
   delivering to the engrafted human skin or human skin cells a papillomavirus genomic DNA; and
   maintaining the mammal for sufficient time for a papillomavirus infection to develop in the engrafted human skin or human skin cells.

2. The method as in claim 1, wherein the mammal is a rodent.

3. The method as in claim 2, wherein the rodent is a mouse.

4. The method as in claim 3, wherein the mouse is a scid/scid mouse.

5. The method as in claim 1, wherein the human skin is human foreskin.

6. The method as in claim 1, wherein the papillomavirus is a human papillomavirus.

7. The method as in claim 6, wherein the human papilloma virus is HPV16.

8. A non-human mammal prepared in accordance with claim 1.

9. A non-human mammal comprising an engrafted portion of human skin, wherein the human skin portion exhibits papillomavirus induced wart formation.

10. The mammal as in claim 9, wherein the papillomavirus is a human papillomavirus.

11. The mammal as in claim 10, wherein the human papilloma virus is HPV16.

12. The mammal as in claim 9, wherein the human skin is human foreskin.

13. A method for producing a mouse model for papillomavirus infection, the method comprising:
   providing a transplant-tolerant mouse;
   excising from the mouse a portion of skin at a graft site;
   engrafting a portion of human foreskin into the graft site, wherein the human foreskin is not infected with papillomavirus;

delivering to the engrafted human foreskin a papillomavirus genomic DNA; and maintaining the mouse for sufficient time for a papillomavirus infection to develop in the engrafted human foreskin.

14. A non-human mammal comprising an engrafted portion of human skin, wherein a human papillomavirus DNA has been administered to the human skin portion after engraftment, and wherein the skin portion exhibits phenotypical characteristics of human papillomavirus induced disease.

15. The mammal as in claim 14, wherein the human papilloma virus is HPV16.

16. The mammal as in claim 14, wherein the human skin is human foreskin.

17. The mammal as in claim 14, wherein the disease is papillomatous lesion.

18. The mammal as in claim 14, wherein the disease is hyperplasia.

19. The mammal as in claim 14, wherein the mammal is a rodent.

20. The mammal as in claim 19, wherein the rodent is a mouse.

21. The mammal as in claim 20, wherein the mouse is a scid/scid mouse.

22. A method for testing an agent for therapeutic activity against a symptom of human papilloma induced disease, the method comprising:

providing a non-human mammal comprising an engrafted portion of human skin, wherein a human papillomavirus DNA has been administered to the human skin portion after engraftment, and wherein the skin portion exhibits a symptom of human papillomavirus induced disease;

administering the agent to the mammal; and evaluating the effect of the agent on the disease symptom.

23. The method of claim 22, wherein the disease symptom is a warty lesion.

24. The method of claim 22, wherein the disease symptom is hyperplasia.

25. The method as in claim 22, wherein the mammal is a rodent.

26. The method as in claim 25, wherein the rodent is a mouse.

27. The method as in claim 26, wherein the mouse is a scid/scid mouse.

28. The method as in claim 22, wherein the human skin is human foreskin.

* * * * *